(12) United States Patent
Lee et al.

(10) Patent No.: US 10,478,368 B2
(45) Date of Patent: Nov. 19, 2019

(54) FORCE TRANSMITTING FRAMES AND MOTION ASSISTANCE APPARATUSES INCLUDING THE SAME

(71) Applicant: Samsung Electronics Co., Ltd., Suwon-si, Gyeonggi-do (KR)

(72) Inventors: Younbaek Lee, Yongin-si (KR); Byungjune Choi, Gunpo-si (KR); Jeonghun Kim, Hwaseong-si (KR); Se-Gon Roh, Suwon-si (KR); Minhyung Lee, Anyang-si (KR); Jongwon Lee, Uiwang-si (KR); Hyundo Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1113 days.

(21) Appl. No.: 14/843,039

(22) Filed: Sep. 2, 2015

(65) Prior Publication Data

US 2016/0081870 A1    Mar. 24, 2016

(30) Foreign Application Priority Data

Sep. 19, 2014 (KR) ........................ 10-2014-0125240
Jun. 2, 2015 (KR) ........................ 10-2015-0078098

(51) Int. Cl.
*A61H 1/00* (2006.01)
*A61H 1/02* (2006.01)
(Continued)

(52) U.S. Cl.
CPC ............ *A61H 1/008* (2013.01); *A61F 2/605* (2013.01); *A61F 5/0102* (2013.01);
(Continued)

(58) Field of Classification Search
CPC ............ A63B 22/0046; A63B 22/0235; A63B 69/0064; A63B 2220/52;
(Continued)

(56) References Cited

U.S. PATENT DOCUMENTS 7,431,708 B2   10/2008   Sreeramagiri
7,479,122 B2   1/2009   Ceriani et al.
(Continued)

FOREIGN PATENT DOCUMENTS

CN   101103949 A   1/2008
CN   101132753 A   2/2008
(Continued)

OTHER PUBLICATIONS

European Patent Office Extended Search Report dated Feb. 1, 2016, Application No. 15186084.8-1658.
(Continued)

*Primary Examiner* — Sundhara M Ganesan
(74) *Attorney, Agent, or Firm* — Harness, Dickey & Pierce, P.L.C.

(57) ABSTRACT

A force transmitting frame may have a length greater than a width. Stiffnesses of first and second end portions of the force transmitting frame may be greater than a stiffness of a central area of the force transmitting frame in a longitudinal direction of the force transmitting frame. The force transmitting frame may include: an inner frame configured to support one side of a user; and/or an outer frame of which first and second end portions are fixed to first and second end portions of the inner frame, and of which a central portion is not fixed to a central portion of the inner frame. The central portion of the outer frame may be configured to slide with respect to the central portion of the inner frame.

36 Claims, 20 Drawing Sheets

(51) Int. Cl.
  *A61H 3/00* (2006.01)
  *A61F 2/60* (2006.01)
  *A61F 5/01* (2006.01)
(52) U.S. Cl.
  CPC .............. *A61H 1/0244* (2013.01); *A61H 3/00* (2013.01); *A61F 2005/0137* (2013.01); *A61F 2005/0165* (2013.01); *A61F 2005/0179* (2013.01); *A61H 2201/1215* (2013.01); *A61H 2201/164* (2013.01); *A61H 2201/165* (2013.01); *A61H 2201/1628* (2013.01)
(58) Field of Classification Search
  CPC ........ A63B 2071/0652; A63B 2225/50; A63B 2220/50; A63B 2022/0094; A63B 21/4009; A61H 3/008; A61H 3/00; A61B 5/112
  See application file for complete search history.

(56) References Cited

U.S. PATENT DOCUMENTS

| | | |
|---|---|---|
| 7,867,183 B2 | 1/2011 | Kazmierczak et al. |
| 8,517,965 B2 | 8/2013 | Doty et al. |
| 8,652,075 B2 | 2/2014 | Takahashi et al. |
| 8,672,864 B2 | 3/2014 | Nordt, III et al. |
| 2005/0203514 A1 | 9/2005 | Jahng et al. |
| 2009/0287125 A1* | 11/2009 | Einarsson ............. A61F 5/0106 602/23 |
| 2011/0218466 A1 | 9/2011 | Takahashi et al. |

FOREIGN PATENT DOCUMENTS

| | | |
|---|---|---|
| CN | 101316567 A | 12/2008 |
| CN | 101862256 A | 10/2010 |
| CN | 102245150 A | 11/2011 |
| CN | 200880004649 | 5/2012 |
| EP | 1005297 A1 | 6/2000 |
| JP | 2010-110464 A | 5/2010 |
| JP | 4603479 B2 | 12/2010 |
| JP | 5411003 B2 | 2/2014 |
| KR | 100950060 B1 | 4/2010 |
| WO | WO-2014/092162 A1 | 6/2014 |

OTHER PUBLICATIONS

Chinese Office Action issued by the Chinese Patent Office dated Jun. 20, 2018 for CN Patent Application No. 201510602921.X (with English translation).

Notice of Rejection for corresponding Japanese Application No. 2015-165489 dated Feb. 19, 2019 and English translation thereof.

* cited by examiner

600

FORCE TRANSMITTING FRAMES AND MOTION ASSISTANCE APPARATUSES INCLUDING THE SAME

CROSS-REFERENCE TO RELATED APPLICATION(S)

This application claims priority from Korean Patent Application No. 10-2014-0125240, filed on Sep. 19, 2014, and Korean Patent Application No. 10-2015-0078098, filed on Jun. 2, 2015, in the Korean Intellectual Property Office (KIPO), the entire contents of which are incorporated herein by reference.

BACKGROUND

1. Field

Some example embodiments may relate generally to force transmitting frames. Some example embodiments may relate generally to motion assistance apparatuses including force transmitting frames.

2. Description of Related Art

With the onset of rapidly aging societies, a number of people may experience inconvenience and/or pain from joint problems. Thus, there may be a growing interest in motion assistance apparatuses enabling the elderly and/or patients having joint problems to walk with less effort. The motion assistance apparatuses may include active joint structures, including hydraulic systems and/or driving motors, to drive each joint portion to assist and/or improve muscular strength of legs of the users.

The users may wear the motion assistance apparatuses over the users' clothing.

Although some example embodiments will be described with relation to driving modules and motion assistance apparatuses for humans, those skilled in the art will appreciate that some example embodiments may be applied to other types of modules, apparatuses, and systems, such as driving modules and motion assistance apparatuses for animals, or more general purpose systems.

SUMMARY

Some example embodiments may provide force transmitting frames.

Some example embodiments may provide motion assistance apparatuses.

Some example embodiments may provide motion assistance apparatuses including force transmitting frames.

In some example embodiments, a force transmitting frame may have a length greater than a width. Stiffnesses of first and second end portions of the force transmitting frame may be greater than a stiffness of a central area of the force transmitting frame in a longitudinal direction of the force transmitting frame.

In some example embodiments, the central area may be flexible.

In some example embodiments, the stiffnesses of the first and second end portions may be 1.5 to 20 times greater than the stiffness of the central area.

In some example embodiments, the stiffnesses of the first and second end portions may be 4 to 10 times greater than the stiffness of the central area.

In some example embodiments, surfaces of the first and second end portions may face a same direction.

In some example embodiments, surfaces of the first and second end portions may face different directions.

In some example embodiments, the surfaces of the first and second end portions may form an angle of 80 degrees to 100 degrees.

In some example embodiments, the central area may be provided in a form of a twisted curve.

In some example embodiments, the force transmitting frame may comprise: an inner frame configured to support one side of a user; and/or an outer frame of which first and second end portions are fixed to first and second end portions of the inner frame, and of which a central portion is not fixed to a central portion of the inner frame. The central portion of the outer frame may be configured to slide with respect to the central portion of the inner frame.

In some example embodiments, the inner frame may comprise an inner plate and a first hanging portion between the inner plate and an outer plate. The outer frame may comprise the outer plate and a second hanging portion configured to fasten to the first hanging portion.

In some example embodiments, one of the first hanging portion and the second hanging portion may comprise a portion having a width increasing in a direction toward the other of the first hanging portion and the second hanging portion.

In some example embodiments, a cross-section of the one hanging portion may correspond to a reversed trapezoidal shape.

In some example embodiments, the inner frame may further comprise a first protruding portion configured to protrude from the inner plate toward the outer plate. The outer frame may further comprise a second protruding portion configured to protrude from the outer plate toward the inner plate.

In some example embodiments, a plurality of first protruding portions may be formed in a longitudinal direction of the inner frame. A plurality of second protruding portions are formed in a longitudinal direction of the outer frame.

In some example embodiments, an interval between two adjacent first protruding portions, among the plurality of first protruding portions, may be configured to be shorter than a length of a second protruding portion provided on an opposite side of the two first protruding portions.

In some example embodiments, an interval between the inner plate and the outer plate may decrease from the central area of the force transmitting frame toward the first and second end portions of the force transmitting frame.

In some example embodiments, an interval between the inner plate and the outer plate may be determined based on the following equation, $h(x)=F(L-x)/[T-F \sin(a \tan(d/dx\, p(x)))]$, wherein '$h(x)$' denotes the interval between the inner plate and the outer plate, '$F$' denotes a magnitude of a force applied to one end portion of the force transmitting frame, '$T$' denotes a magnitude of a tensile force applied to the inner plate, '$L$' denotes a length of the force transmitting frame, '$x$' denotes a distance from an end portion of the force transmitting frame to a desired point of the inner plate, and '$p(x)$' denotes a height of the inner plate at the distance $x$.

In some example embodiments, the force transmitting frame may further comprise: a frame stiffener provided on at least one of the inner frame and the outer frame.

In some example embodiments, the frame stiffener may comprise a carbon fiber material.

In some example embodiments, the force transmitting frame may further comprise: an applying portion connected to one end of the inner frame and one end of the outer frame, and/or configured to transmit a force to a portion of the user.

In some example embodiments, a thickness of the applying portion may be configured to be greater than a sum of a thickness of the one end of the inner frame and a thickness of the one end of the outer frame.

In some example embodiments, a distance between the inner plate and the outer plate may increase as a distance from the applying portion increases.

In some example embodiments, a force transmitting frame may comprise: a first plate; a second plate configured to face the first plate; a connecting portion configured to connect one end of the first plate to one end of the second plate; and/or an applying portion configured to connect a second end of the first plate to a second end of the second plate.

In some example embodiments, the force transmitting frame may further comprise: a separation preventing member configured to prevent separation between the first plate and the second plate.

In some example embodiments, a first side of the separation preventing member may be slidingly connected to the first plate, and a second side of the separation preventing member may be slidingly connected to the second plate.

In some example embodiments, the force transmitting frame may further comprise: a guide portion comprising a guide protrusion configured to protrude from the first plate, and a guide hole provided in the guide protrusion. The second plate may be configured to be received in the guide hole.

In some example embodiments, an interval between the first plate and the second plate may be determined in proportion to a value obtained by multiplying an inner product of a first unit vector of a normal direction of the applying portion and a second unit vector of a direction of the interval by a distance value from the applying portion to the interval.

In some example embodiments, an interval between the first plate and the second plate may be determined in proportion to a distance in a direction perpendicular to a direction of a force applied to the applying portion.

In some example embodiments, a motion assistance apparatus may comprise: a fixing member to be attached to a user; a driving source provided on one side of the fixing member; a joint assembly configured to assist rotary motion of a joint portion of the user; and/or a force transmitting frame of which a first end portion is connected to the joint assembly, and of which a second end portion is configured to transmit a force to a portion of the user. A stiffness of the second end portion of the force transmitting frame may be greater than a stiffness of a central portion of the force transmitting frame.

In some example embodiments, the force transmitting frame may comprise first and second plates. First and second end portions of the first plate may be fixed to first and second end portions of the second plate. A central portion of the first plate may not be fixed to a central portion of the second plate.

In some example embodiments, the stiffness of the second end portion of the force transmitting frame may be 1.5 to 20 times greater than the stiffness of the central portion of the force transmitting frame.

In some example embodiments, the stiffness of the second end portion of the force transmitting frame may be 4 to 10 times greater than the stiffness of the central portion of the force transmitting frame.

In some example embodiments, the force transmitting frame may further comprise: a supporting body, between the inner frame and the outer frame, configured to support the inner frame and the outer frame; and/or a separation preventing band configured to prevent separation of the inner frame and the outer frame from one another.

In some example embodiments, the supporting body may be vertically bent a plurality of times. The supporting body may comprise carbon fiber. The separation preventing band may be wound around circumferences of the inner frame and the outer frame. The separation preventing band may comprise fabric material.

In some example embodiments, the force transmitting frame may further comprise: a supporting body, between the first plate and the second plate, configured to support the first plate and the second plate; and/or a separation preventing band configured to prevent separation of the first plate and the second plate from one another.

In some example embodiments, the force transmitting frame may further comprise: a supporting body, between the first and second plates, configured to support the first and second plates; and/or a separation preventing band configured to prevent separation of the first and second plates from one another.

In some example embodiments, a force transmitting frame may comprise: a first plate; a second plate; and/or a middle portion configured to prevent separation of the first plate from the second plate. A stiffness of a first end portion of the force transmitting frame may be greater than a stiffness of a central area of the force transmitting frame. A stiffness of a second end portion of the force transmitting frame may be greater than the stiffness of the central area of the force transmitting frame.

In some example embodiments, the middle portion may be part of the first plate.

In some example embodiments, the middle portion may be part of the first plate and the second plate.

In some example embodiments, the middle portion may not be part of the first plate or the second plate.

In some example embodiments, the stiffness of the first end portion may be 1.5 to 20 times greater than the stiffness of the central area.

In some example embodiments, the stiffness of the first end portion may be 4 to 10 times greater than the stiffness of the central area.

In some example embodiments, the stiffnesses of the first and second end portions may be 4 to 10 times greater than the stiffness of the central area.

In some example embodiments, surfaces of the first and second end portions may face a same direction.

In some example embodiments, surfaces of the first and second end portions may face different directions.

Additional aspects of example embodiments will be set forth in part in the description which follows and, in part, will be apparent from the description, or may be learned by practice of the disclosure.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
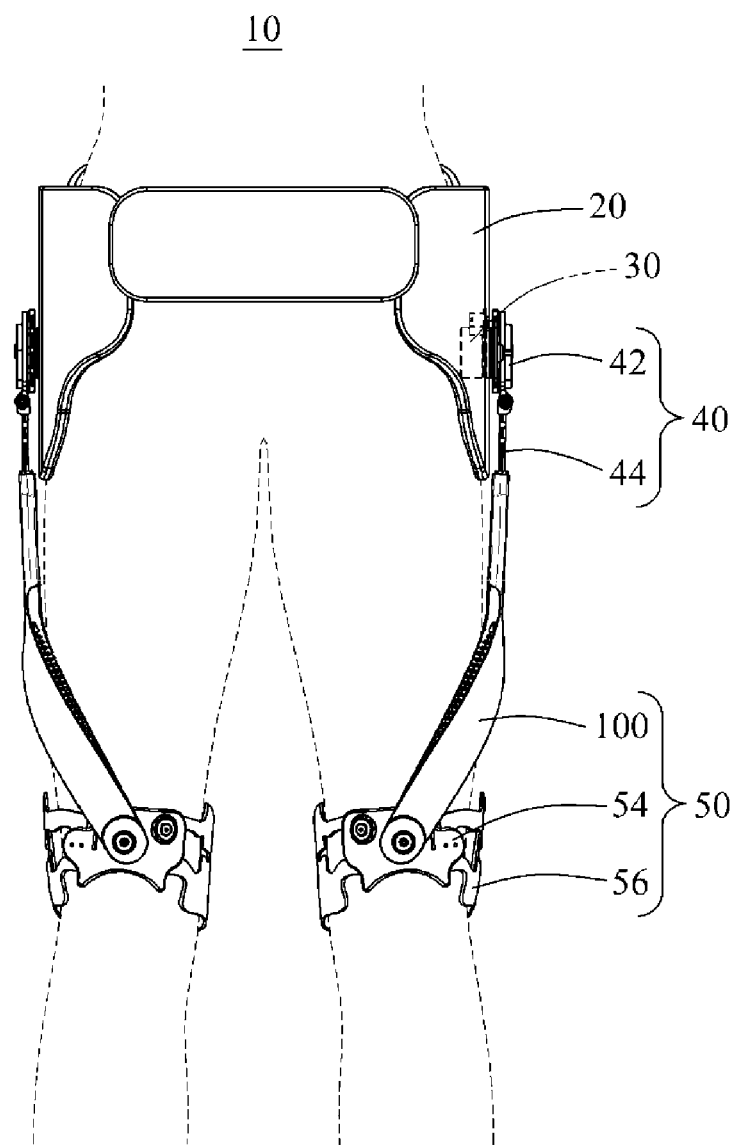
FIG. 1 is a front view illustrating a motion assistance apparatus according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
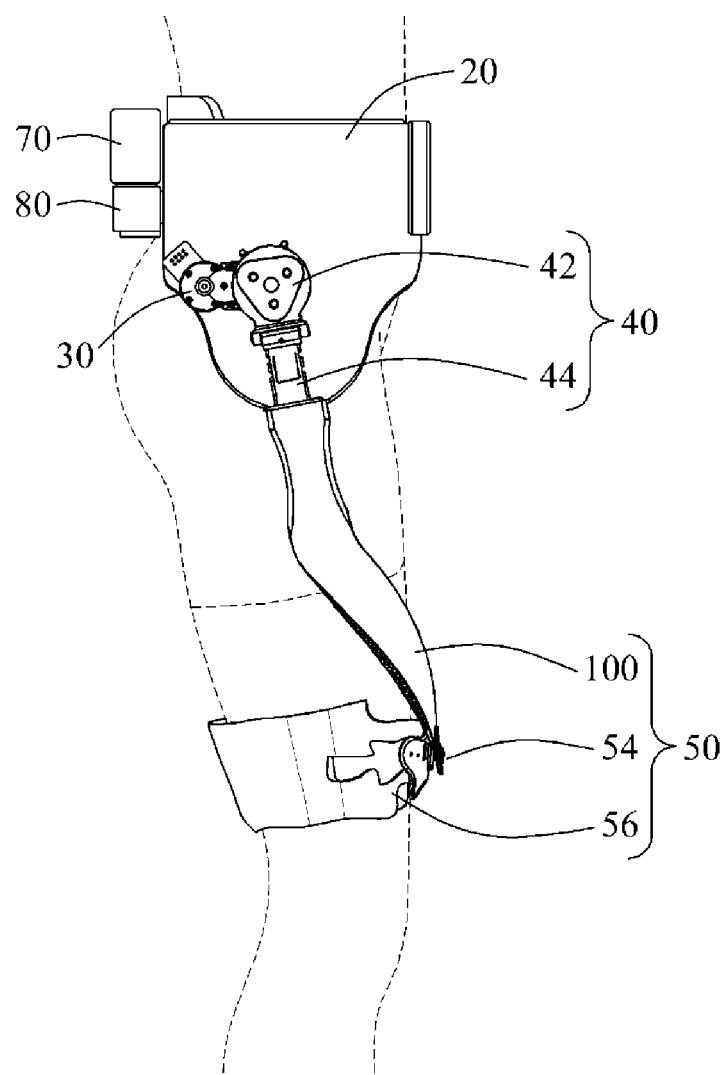
FIG. 2 is a side view illustrating a motion assistance apparatus according to some example embodiments.

FIG. 1 is a front view illustrating a motion assistance apparatus 10 according to some example embodiments, and FIG. 2 is a side view illustrating the motion assistance apparatus 10 according to some example embodiments.

Referring to FIGS. 1 and 2, the motion assistance apparatus 10 may be worn by a user to assist a motion of the user.

The user may be a human, an animal, or a robot. However, example embodiments are not limited thereto. Further, although FIG. 1 illustrates a case in which the motion assistance apparatus 10 assists a motion of a thigh of the user, the motion assistance apparatus 10 may also assist a motion of another part of an upper body, for example, a hand, an upper arm, and a lower arm of the user, or a motion of another part of a lower body, for example, a foot and a calf of the user. The motion assistance apparatus 10 may assist a motion of a part of the user.

In some example embodiments, a motion assistance apparatus for a robot could establish a master/slave or slave/master relationship between the motion assistance apparatus and robot. Such a master device may not be a single device, but may include more than one device, each performing one or more functions of the master device (e.g., the functionality of the master device may be distributed). Similarly, the slave device may not be a single device, but may include more than one device, each performing one or more functions of the slave device (e.g., the functionality of the slave device may be distributed). Therefore, the functionality of the master device, the slave device, or the master and slave devices may be distributed.

In some example embodiments, in such master/slave or slave/master relationship, the master device may be required to perform certain functions, but may or may not perform other functions while maintaining its role as the master device. One or more of these other functions may be shared with or performed by the slave device (which maintains its role as the slave device). Similarly, the slave device may be required to perform certain functions, but may or may not perform other functions while maintaining its role as the slave device. One or more of those other functions may be shared with or performed by the master device (which maintains its role as the master device). Thus, the required functionality of the master and slave devices may be maintained, while functionality that may be shared with or performed by the other device may be so shared with or performed by the other device consistent with the master device maintaining its role as the master device and the slave device maintaining its role as the slave device.

Although FIG. 1 illustrates a case in which the motion assistance apparatus 10 is a two-sided embodiment, in some example embodiments, the motion assistance apparatus 10 may be a one-sided embodiment.

Although FIG. 1 illustrates a case in which the motion assistance apparatus 10 may assist a motion of both thighs of the user, in some example embodiments, the motion assistance apparatus 10 may also assist a motion of only one thigh of a user at a time.

Hereinafter, a case in which the motion assistance apparatus 10 assists a motion of a thigh of a human will be described as an example.

The motion assistance apparatus 10 may include a fixing member 20, a driving module 30, a joint assembly 40, a supporting module 50, a controller 70 configured to control the driving module 30, and a power supply unit 80 configured to supply power to the driving module 30.

The fixing member 20 may be attached to the user, and configured to cover an external surface of the user. For example, the fixing member 20 may be attached to one side of a waist of the user, and include a curved surface corresponding to a contact portion of the user.

The driving module 30 may provide power to be transmitted to the joint assembly 40. The driving module 30 may include a motor configured to receive voltage or current from the power supply unit 80 and to generate power. For example, the driving module 30 may be disposed in a lateral direction of the joint assembly 40, in detail, such that an axis of rotation of the driving module 30 may be spaced apart from an axis of rotation of the joint assembly 40. In some example embodiments, when compared to a case in which the driving module 30 and the joint assembly 40 share an axis of rotation, a protruding height from the user may relatively decrease. In addition, the driving module 30 may be disposed to be spaced apart from the joint assembly 40 even further. In some example embodiments, a power transmitting module (not shown) may be additionally provided to transmit power from the driving module 30 to the joint assembly 40. The power transmitting module may be a rotary body such as, for example, a gear, or a longitudinal member such as, for example, a wire, a cable, a string, a rubber band, a spring, a belt, or a chain.

The joint assembly 40 may receive power from the driving module 30, and may assist a motion of a joint portion of the user. The joint assembly 40 may be disposed on one side of the fixing member 20 at a position corresponding to the joint portion of the user. One side of the joint assembly 40 may be connected to the driving module 30, and another side of the joint assembly 40 may be connected to the supporting module 50.

The joint assembly 40 may include a rotating member 42 and a connecting member 44. The rotating member 42 may rotate using power received from the driving module 30. For example, the rotating member 42 may be disposed on one side of a hip joint of the user. The connecting member 44 may connect the rotating member 42 to the supporting module 50, and may rotate using torque of the rotating member 42. The connecting member 44 may be provided, for example, in a hinge connection structure. By a hinge axis of the hinge connection structure and an axis of rotation of the rotating member 42, the supporting module 50 may perform a two degree of freedom (DOF) motion with respect to the fixing member 20.

The supporting module 50 may support a portion of the user, and may assist a motion of the portion of the user. The supporting module 50 configured to rotate using torque of the joint assembly 40 may include a force transmitting frame 100, an applying member 54, and a supporting member 56.

The force transmitting frame 100 may transmit force to a portion of the user. One end portion of the force transmitting frame 100 may be rotatably connected to the joint assembly 40, and another end portion of the force transmitting frame 100 may be connected to the supporting member 56 to transmit force to a portion of the user. For example, the force transmitting frame 100 may push or pull a thigh of the user. The force transmitting frame 100 may extend and be bent in a longitudinal direction of the thigh of the user to cover at least a portion of the circumference of the thigh of the user. The one end portion of the force transmitting frame 100 may be disposed on a side surface of the thigh of the user, and the other portion of the force transmitting frame 100 may be disposed on a front surface of the thigh of the user. A surface on the side of the one end portion of the force transmitting frame 100 may be orthogonal to a surface on the side of the other end portion of the force transmitting frame 100.

The force transmitting frame 100 may be movably connected to the connecting member 44. By relative motions of the force transmitting frame 100 and the connecting member 44, a total length from the joint assembly 40 to the applying member 54 may be variable. In some example embodiments, the supporting module 50 may perform a three DOF motion with respect to the fixing member 20.

The applying member 54 may be connected to the other end portion of the force transmitting frame 100 to apply force to a portion of the user. For example, the applying member 54 may be disposed along the front surface of the thigh of the user, or in a circumferential direction of the thigh of the user to push or pull the thigh of the user. The applying member 54 may include a curved surface corresponding to the thigh of the user, and configured to extend from the other end portion of the force transmitting frame 100 toward both sides of the force transmitting frame 100.

The supporting member 56 may be connected to one side of the applying member 54. For example, the supporting member 56 may be disposed to cover a circumference of at least a portion of the thigh of the user, thereby preventing separation between the thigh of the user and the force transmitting frame 100.

Figure 3:
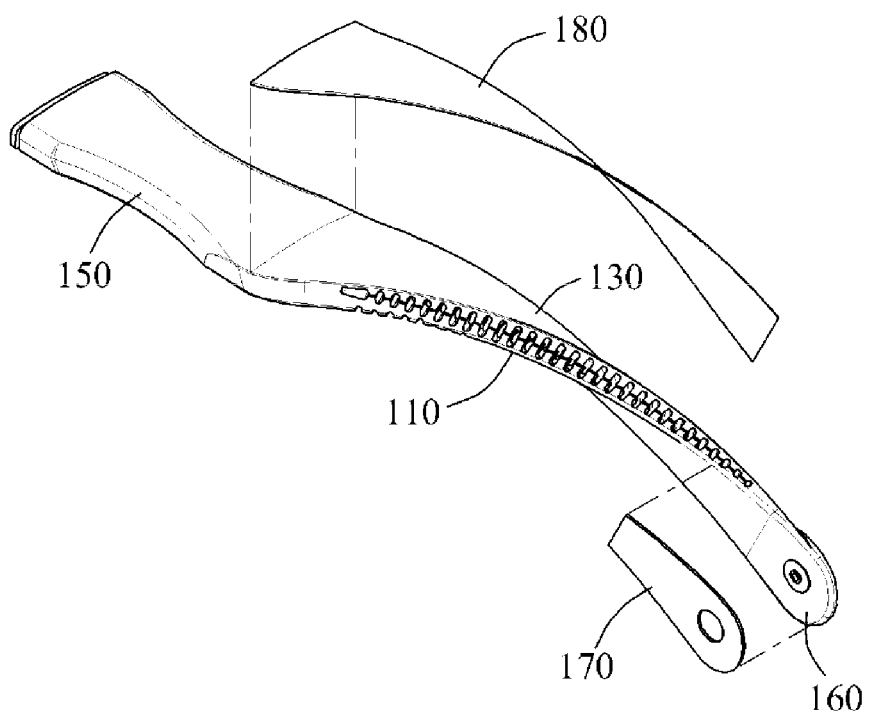
FIG. 3 is an exploded perspective view illustrating a force transmitting frame according to some example embodiments.
Figure 4:
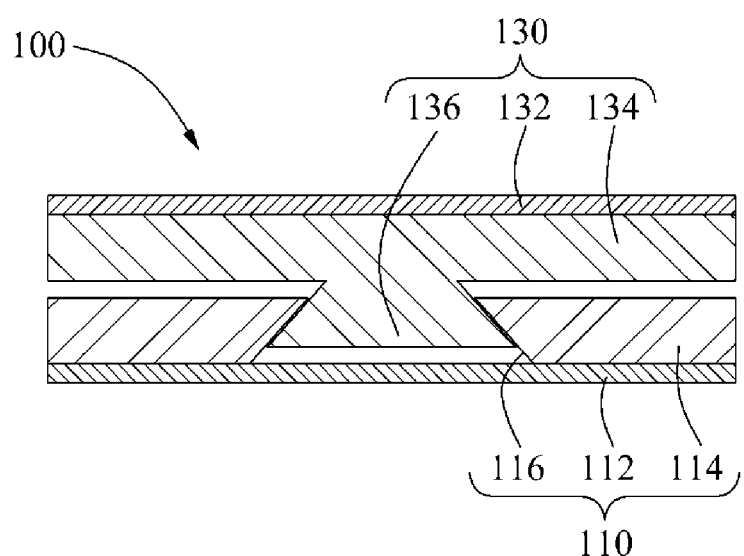
FIG. 4 is a cross-sectional view illustrating a force transmitting frame according to some example embodiments.

FIG. 3 is an exploded perspective view illustrating the force transmitting frame 100 according to some example embodiments, and FIG. 4 is a cross-sectional view illustrating the force transmitting frame 100 according to some example embodiments.

Referring to FIGS. 3 and 4, the force transmitting frame 100 may include an inner frame 110, an outer frame 130, a joint connecting portion 150, and an applying portion 160. The force transmitting frame 100 may include optional frame stiffeners 170 and 180.

The inner frame 110 may be disposed to face a user and support one side of the user. As shown in FIG. 1, the inner frame 110 may support a side surface of a thigh in the vicinity of a pelvis of the user, and may support a front surface of the thigh in the vicinity of a knee of the user. To support the side surface and the front surface of the thigh of the user, a central area of the inner frame 110 may be implemented in a form of a twisted curve. The inner frame 110 may also be referred to as a first frame. The inner frame 110 may include an inner plate 112, a first protruding portion 114, and a first hanging portion 116.

The inner plate 112 may be provided in a shape corresponding to an external surface of the user. For example, as described above, the inner plate 112 may be disposed lengthwise in a form corresponding to the side surface of the thigh in the vicinity of the pelvis of the user and the front surface of the thigh in the vicinity of the knee of the user in a longitudinal direction of the thigh of the user. The inner plate 112 may be formed using a thin elastic board, for example, a material such as plastic or steel. The inner plate 112 may also be referred to as a first plate.

The first protruding portion 114 may protrude from the inner plate 112 toward the outer frame 130. A plurality of first protruding portions 114 may be disposed to be spaced apart from each other in a longitudinal direction of the inner plate 112, and formed lengthwise in a circumferential direction of the thigh of the user, the circumferential direction corresponding to a direction orthogonal to the longitudinal direction of the inner plate 112.

The first hanging portion 116 may prevent a separation of the outer frame 130 from the inner frame 110. The first hanging portion 116 may be provided in a form of a groove including side surfaces of the first protruding portions 114 and an internal surface of the inner plate 112. As shown in FIG. 4, the first hanging portion 116 may be provided in a form of a trapezoidal groove. To achieve such a groove form, the side surfaces of the first protruding portions 114 may protrude inwardly as a distance from the inner plate 112 increases. For example, when the first protruding portions 114 are arranged in two rows along edges of both sides of the inner plate 112, the side surfaces of the first protruding portions 114 may protrude toward a center as the distance from the inner plate 112 increases. The side surfaces of the first protruding portions 114 and the internal surface of the inner plate 112 may form a groove that may be fastened to a second hanging portion 136 of the outer frame 130, thereby preventing the separation between the inner frame 110 and the outer frame 130.

The outer frame 130 may be provided in a shape corresponding to the inner frame 110. The outer frame 130 may be disposed in an opposite direction of the user with respect to the inner frame 110. The outer frame 130 may also be referred to as a second frame. The outer frame 130 may include an outer plate 132, a second protruding portion 134, and the second hanging portion 136.

The outer plate 132 may be disposed to be spaced apart from the inner plate 112 in a shape corresponding to the inner plate 112. The outer plate 132 may be formed using a thin elastic board, for example, a material such as plastic or steel. The outer plate 132 may also be referred to as a second plate.

An interval between the outer plate 132 and the inner plate 112 may increase as a distance from the applying portion 160 and/or the joint connecting portion 150 increases. For example, the interval may be maximized at a central portion of the force transmitting frame 100, and decrease gradually toward both end portions thereof. Thus, stiffnesses of the both end portions of the force transmitting frame 100 may be greater than a stiffness of the central portion thereof.

When the force transmitting frame 100 has a three-dimensional (3D) shape, the interval between the outer plate 132 and the inner plate 112 may be determined in proportion to a value obtained by multiplying an inner product of a first unit vector of a normal direction of the applying portion 160 and a second unit vector of a direction of the interval by a distance value from the applying portion 160 to the interval.

The second protruding portion 134 may protrude from the outer plate 132 toward the inner plate 112. A plurality of second protruding portions 134 may be disposed to be spaced apart from each other in a longitudinal direction of the outer plate 132, and formed lengthwise in a circumferential direction of the thigh of the user, the circumferential direction orthogonal to the longitudinal direction of the outer plate 132.

The second hanging portion 136 may prevent a separation of the inner frame 110 from the outer frame 130. As shown in FIG. 4, a cross-section of the second hanging portion 136 may correspond to a shape of a reversed trapezoidal dovetail. The second hanging portion 136 with a width increasing in a direction from the outer plate 132 toward the inner plate 112 may be fastened to the first hanging portion 116 of a trapezoidal shape, thereby preventing the separation between the inner frame 110 and the outer frame 130.

The joint connecting portion 150 may transmit torque of the joint assembly 40 to the inner frame 110 and the outer frame 130. One end of the inner plate 112 and one end of the outer plate 132 may be fixed to one end of the joint connecting portion 150, and the connecting member 44 of the joint assembly 40 may be fixed to another end of the joint connecting portion 150.

The applying portion 160 may receive the torque of the joint assembly 40 and transmit force to a portion of the user. As shown in FIG. 1, to enable the applying portion 160 to transmit force to the front surface of the thigh of the user, another end of the inner plate 112 and another end of the outer plate 132 may be fixed to the applying portion 160. A thickness of the applying portion 160 may be greater than a sum of thicknesses of the inner frame 110 and the outer frame 130 that are adjacent to the applying portion 160.

A surface of the joint connecting portion 150 and a surface of the applying portion 160 of the force transmitting frame 100 may face different directions. As shown in FIG. 3, the force transmitting frame 100 may be provided in a structure in which the surface of the joint connecting portion 150 faces the side surface of the thigh in the vicinity of the pelvis of the user, and the surface of the applying portion 160 faces the front surface of the thigh in the vicinity of the knee of the user. In detail, the surface of the joint connecting portion 150 and the surface of the applying portion 160 may form an angle of about 80 degrees to about 100 degrees.

The frame stiffeners 170 and 180 may be provided on at least one of the inner frame 110, the outer frame 130, and the applying portion 160. The frame stiffeners 170 and 180 may be added to portions requiring an increase in stiffness, and include a carbon fabric material with relatively great strength and elasticity. For example, the frame stiffeners 170 and 180 may include a carbon fiber reinforced plastic (CFRP) material. The frame stiffeners 170 and 180 also may include other materials, such as carbon-nanotube-reinforced polymer, glass-fiber-reinforced polymer, or aramid-fiber-reinforced polymer.

By the joint connecting portion 150 and the applying portion 160, end portions of the force transmitting frame 100, to which both end portions of the inner frame 110 and the outer frame 130 are fixed, respectively, may have relatively great stiffnesses resistant to a torsion. In addition, a central portion of the inner frame 110 may relatively move with respect to a central portion of the outer frame 130. Thus, a central portion of the force transmitting frame 100 may have a greater flexibility (e.g., low stiffness) than the end portions thereof. Conversely, stiffnesses of the both end portions of the force transmitting frame 100 may be greater than a stiffness of the central portion thereof. In detail, the stiffnesses of the both end portions of the force transmitting frame 100 may be 1.5 to 20 times greater than the stiffness of the central portion thereof. In more detail, the stiffnesses of the both end portions of the force transmitting frame 100 may be 4 to 10 times greater than the stiffness of the central portion thereof. The stiffnesses of the both end portions of the force transmitting frame 100 may be identical to or different from the stiffness of the central portion thereof. In some example embodiments, the stiffness of the central portion of the force transmitting frame 100 may be about 0.91 newtons per millimeter (N/mm), and a stiffness of one end portion of the force transmitting frame 100 may be about 5.9 N/mm.

The separation between the inner frame 110 and the outer frame 130 may be prevented by an interaction between the first hanging portion 116 and the second hanging portion 136. Thus, the central portion of the inner frame 110 may slide with respect to the central portion of the outer frame 130. By the force transmitting frame 100, buckling of the inner frame 110 or the outer frame 130 may be prevented while the central portion of the force transmitting frame 100 is flexible.

A force transmitting frame as described above may be provided lengthwise to have a length greater than a width and a twisted central area, thereby being disposed to extend from a side surface of a thigh in the vicinity of a pelvis of a user to a front surface of the thigh in the vicinity of a knee of the user. Both end portions configured to receive and transmit force may have relatively high stiffnesses, whereas a central portion configured to be in contact with the thigh of the user may have a relatively low stiffness and a flexibility. Thus, a wearability may increase.

In some example embodiments, two frames may be fastened in a form of dovetails to form a flexible central portion. However, other structures may also be applicable. In some example embodiments, by differentiating thicknesses or materials of both end portions and a central portion of a single frame, a difference in stiffness may be implemented. A force transmitting frame including a flexible central area and both end portions stiffer than the central area may belong to the technical category of the present disclosure. In some example embodiments, the stiffnesses of the both end portions may be 1.5 to 20 times, in detail, 4 to 10 times greater than or equal to the stiffness of the central area, or may be identical to or different from the stiffness of the central area.

Figure 5:
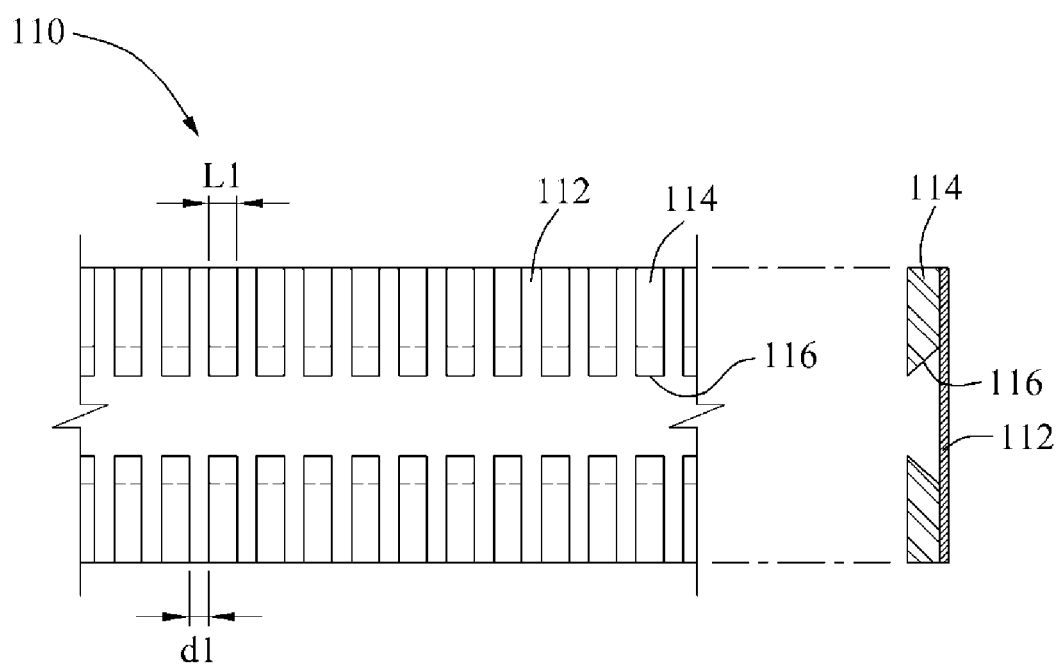
FIG. 5 is a view illustrating an internal surface and a side surface of an inner frame according to some example embodiments.
Figure 6:
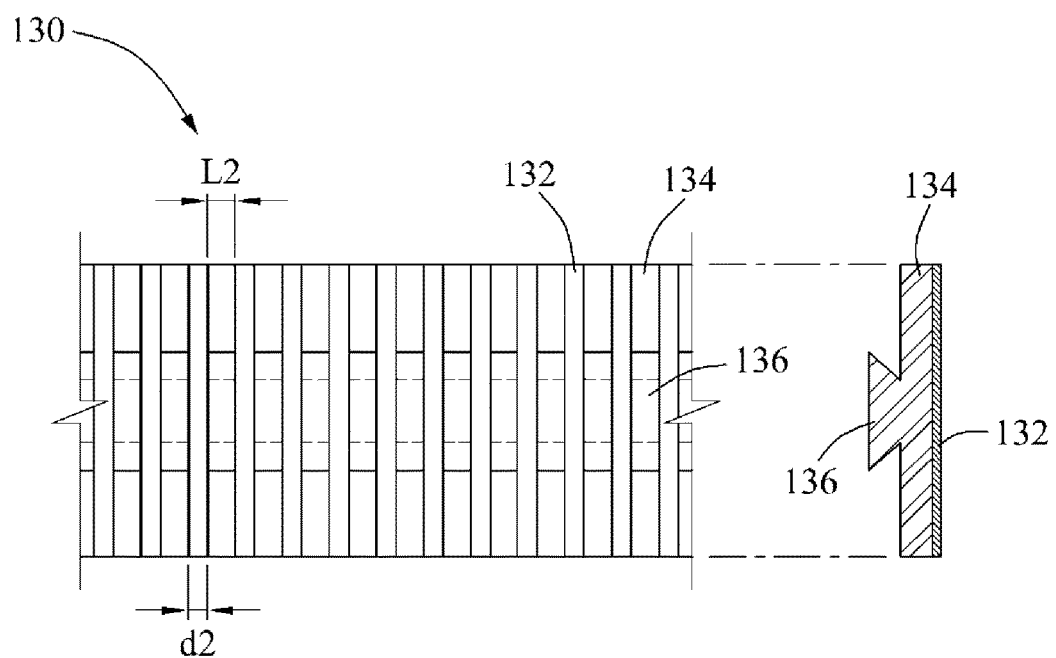
FIG. 6 is a view illustrating an internal surface and a side surface of an outer frame according to some example embodiments.
Figure 7A:
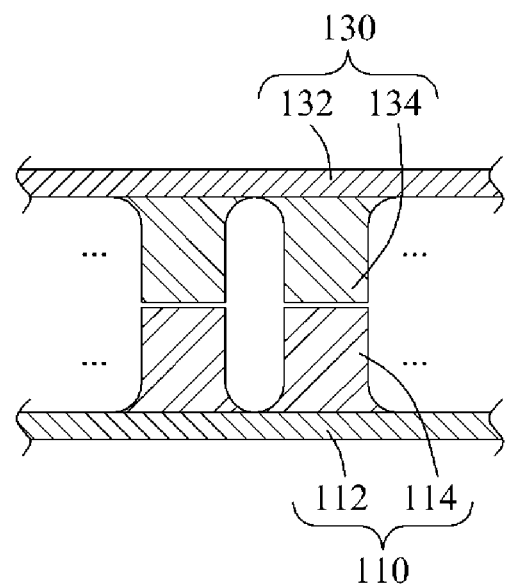
FIGS. 7A through 7C are views illustrating a sliding movement in a portion of a force transmitting frame according to some example embodiments.
Figure 7B:
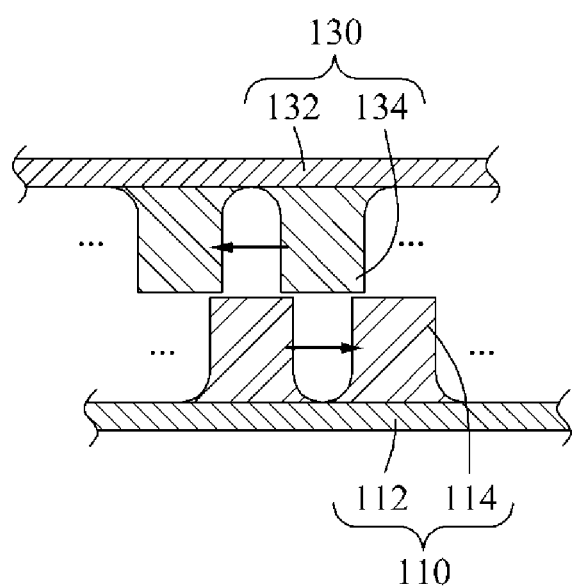
Figure 7C:
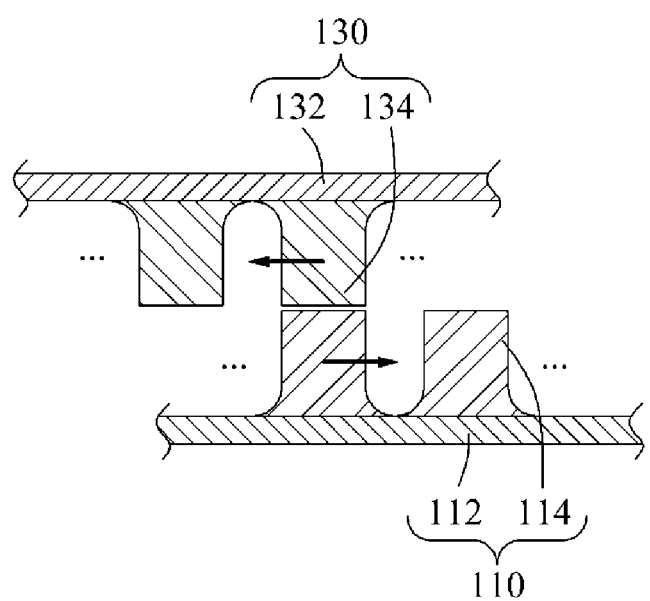

FIG. 5 is a view illustrating an internal surface and a side surface of the inner frame 110 according to some example embodiments, FIG. 6 is a view illustrating an internal surface and a side surface of the outer frame 130 according to some example embodiments, and FIGS. 7A through 7C are views illustrating a sliding movement in a portion of the force transmitting frame 100 according to some example embodiments. When force is applied to a central portion of the force transmitting frame 100, a sliding movement may be performed in at least a portion of the force transmitting frame 100, as shown in FIGS. 7A through 7C.

Referring to FIGS. 5 through 7C, when the inner frame 110 and the outer frame 130 slide with respect to each other, the first protruding portion 114 and the second protruding portion 134 may move smoothly, without being engaged with each other.

In detail, an interval d1 between two adjacent first protruding portions 114, among a plurality of first protruding portions 114, may be formed to be shorter than a length L2 of a second protruding portion 134 disposed to face the two adjacent first protruding portions 114. Similarly, an interval d2 between two adjacent second protruding portions 134, among a plurality of second protruding portions 134, may be formed to be shorter than a length L1 of a first protruding portion 114 disposed to face the two adjacent second protruding portions 134. By the foregoing structure, during the sliding movement as shown in FIG. 7, protruding portions may not be inserted into opposite intervals and, thus, the sliding movement may not be interrupted.

In detail, when external force is applied in a state in which external force is not applied to the force transmitting frame 100 as shown in FIG. 7A, the central portion of the inner frame 110 and the central portion of the outer frame 130 may relatively move, as shown in FIGS. 7B and 7C. In the foregoing process, the first protruding portion 114 may move from a position at which the first protruding portion 114 faces a single second protruding portion 134 to a position at which the first protruding portion 114 faces another adjacent second protruding portion 134, without being inserted into an interval between the second protruding portions 134. Thus, the first protruding portion 114 may slide smoothly.

Hereinafter, the same name may be used to describe an element included in some example embodiments described above and an element having a common function. Unless otherwise mentioned, the descriptions on some example embodiments may be applicable to the following example embodiments and, thus, duplicated descriptions will be omitted for conciseness.

Figure 8:
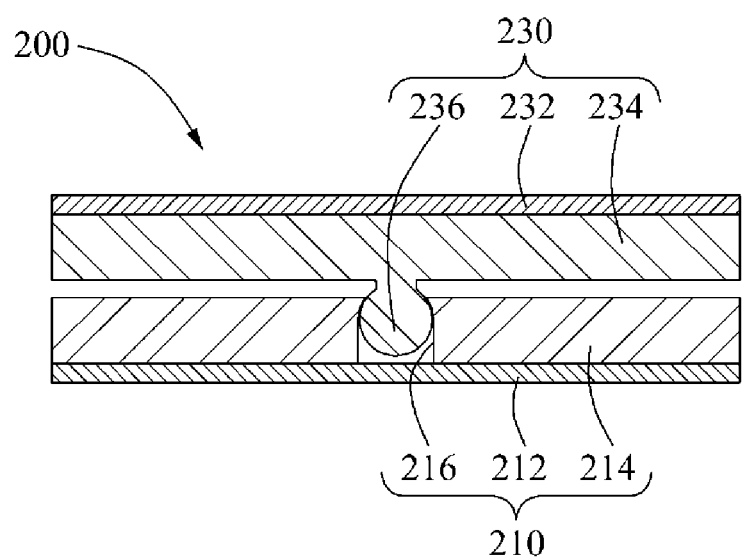
FIG. 8 is a cross-sectional view illustrating a force transmitting frame according to some example embodiments.

FIG. 8 is a cross-sectional view illustrating a force transmitting frame 200 according to some example embodiments.

Referring to FIG. 8, the force transmitting frame 200 may include an inner frame 210 and an outer frame 230. The inner frame 210 may include an inner plate 212, a first protruding portion 214, and a first hanging portion 216. The outer frame 230 may include an outer plate 232, a second protruding portion 234, and a second hanging portion 236.

The second hanging portion 236 may be fastened to the first hanging portion 216. The second hanging portion 236 may include a portion with a width increasing as a distance from the outer plate 232 increases. For example, a cross-section of the second hanging portion 236 may be a circular shape, and a cross-section of the first hanging portion 216 may be a rectangular groove of which two edges are bent inwardly. In some example embodiments, an area to be in contact with the first hanging portion 216 may decrease and, thus, a central portion of the inner frame 210 may slide more smoothly with respect to a central portion of the outer frame 230.

Figure 9:
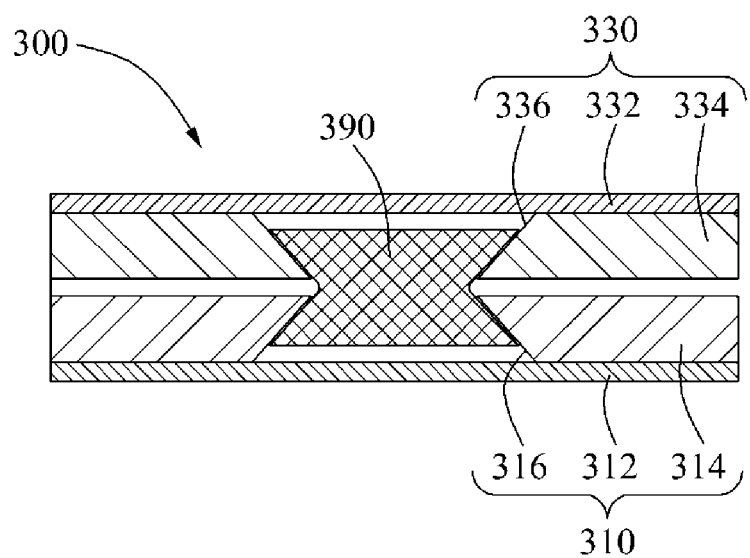
FIG. 9 is a cross-sectional view illustrating a force transmitting frame according to some example embodiments.

FIG. 9 is a cross-sectional view illustrating a force transmitting frame 300 according to some example embodiments.

Referring to FIG. 9, the force transmitting frame 300 may include an inner frame 310, an outer frame 330, and a separation preventing member 390. The inner frame 310 may include an inner plate 312, a first protruding portion 314, and a first hanging portion 316. The outer frame 330 may include an outer plate 332, a second protruding portion 334, and a second hanging portion 336.

The separation preventing member 390 may prevent a separation between the inner plate 312 and the outer plate 332. One side of the separation preventing member 390 may be fastened to the first hanging portion 316, and slide with respect to the first hanging portion 316. For example, the one side of the separation preventing member 390 may have a reversed trapezoidal shape including a portion with a width increasing in a direction toward the inner plate 312. Similarly, another side of the separation preventing member 390 may be fastened to the second hanging portion 336.

The one side and the other side of the separation preventing member 390 may be provided in a shape of two combined reversed trapezoids including portions with widths increasing from a center toward the inner plate 312 and outer plate 332, respectively.

Figure 10:
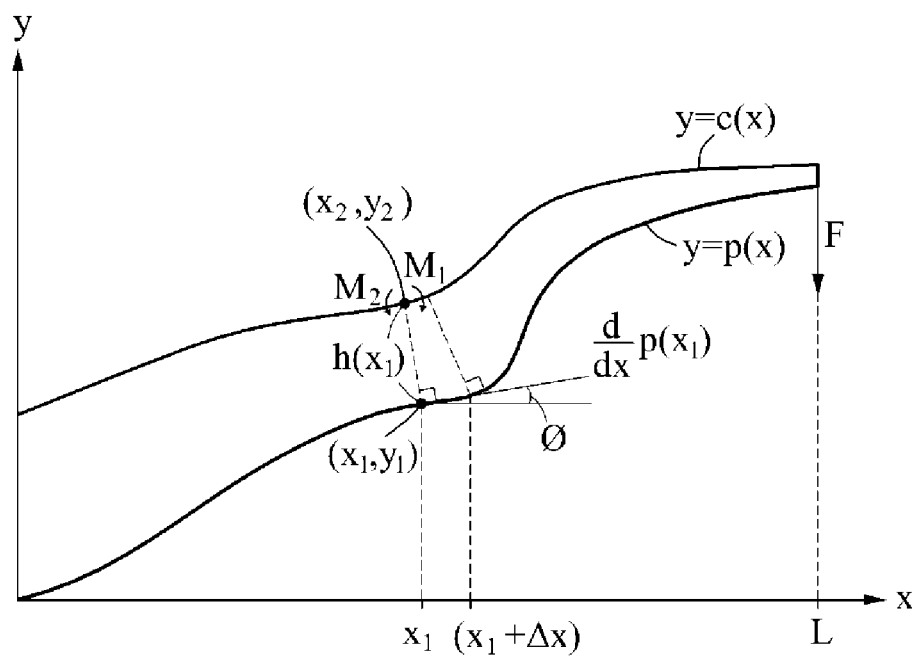
FIG. 10 is a graph illustrating a method of determining an interval of a force transmitting frame according to some example embodiments.

FIG. 10 is a graph illustrating a method of determining an interval between an inner plate and an outer plate according to some example embodiments.

The origin of the graph of FIG. 10 denotes a portion at which a joint connecting portion and an inner plate are connected. When F denotes force applied to an applying portion, the force F may refer to force vertically applied to a front surface of a thigh of a user. When uniform force F is applied to the applying portion, an interval h(x) between the inner plate and the outer plate that prevents buckling of the outer plate may be determined. The interval h(x) may set a sum of moments applied to the outer plate to "0".

A point of the outer plate that meets a normal line at a point (x1, y1) of the inner plate may be (x2, y2). Moments applied to the point (x2, y2) may include a moment M1 applied by the force F, and a moment M2 applied to the inner plate by a tensile force T. A tensile force applied to the outer plate may not apply a moment to the point $(x_2, y_2)$ and, thus, may not be considered. The moments $M_1$ and $M_2$ may be calculated, as expressed by Equations 1 and 2, respectively.

$$M_1 = F(L - x_1 + h(x_1)\sin\Phi) \quad \text{[Equation 1]}$$

$$M_2 = Th(x_1) \quad \text{[Equation 2]}$$

An interval $h(x_1)$ that sets a sum of moments applied to the point $(x_2, y_2)$ to "0" may be determined, as expressed by Equation 3. When the moments $M_1$ and $M_2$ use the same conditions, the interval $h(x_1)$ may be determined, as expressed by Equation 3.

$$h(x_1) = \frac{F(L - x_1)}{T - F\sin\Phi} \quad \text{[Equation 3]}$$

In Equation 3, Φ denotes an angle between a tangent line with respect to a point of the inner plate and an X-axis. When p(x) denotes a height of the inner plate, p(x) may be a function that defines a shape of the inner plate. Similarly, when c(x) denotes a height of the outer plate, c(x) may be a function that defines a shape of the outer plate. A relationship between Φ and p(x) may be expressed by Equation 4.

$$\tan\Phi = \frac{d}{dx}p(x) \quad \text{[Equation 4]}$$

Using Equation 4, Equation 3 may be expressed as Equation 5.

$$h(x_1) = \frac{F(L - x_1)}{T - F\sin\left(\text{atan}\left(\frac{d}{dx}p(x_1)\right)\right)} \quad \text{[Equation 5]}$$

Equation 5 may be generalized as an equation with respect to a desired point (that may or may not be predetermined) (x, y) of the inner plate, as expressed by Equation 6.

$$h(x) = \frac{F(L - x)}{T - F\sin\left(\text{atan}\left(\frac{d}{dx}p(x)\right)\right)} \quad \text{[Equation 6]}$$

In Equation 6, a relationship between T and F may be calculated when the function p(x) with respect to the shape of the inner plate is provided. F denotes a force applied to a portion of a user, and may or may not be predetermined by a user or a designer. Thus, when the function p(x) is provided, a shape of the outer plate to be spaced apart from the inner plate at the interval h(x) may be determined. By using the force transmitting frame determined using the method as described above, the force transmitting frame may not be bent and may transmit a force fully when a load is applied to the applying portion.

When the force transmitting frame has a two-dimensional (2D) shape, the interval between the outer plate and the inner plate may be determined in proportion to a distance in a direction perpendicular to a direction of the force applied to the applying portion.

The description provided above is merely an example embodiment of a method of determining an interval between an inner plate and an outer plate. However, example embodiments are not limited thereto.

Figure 11:
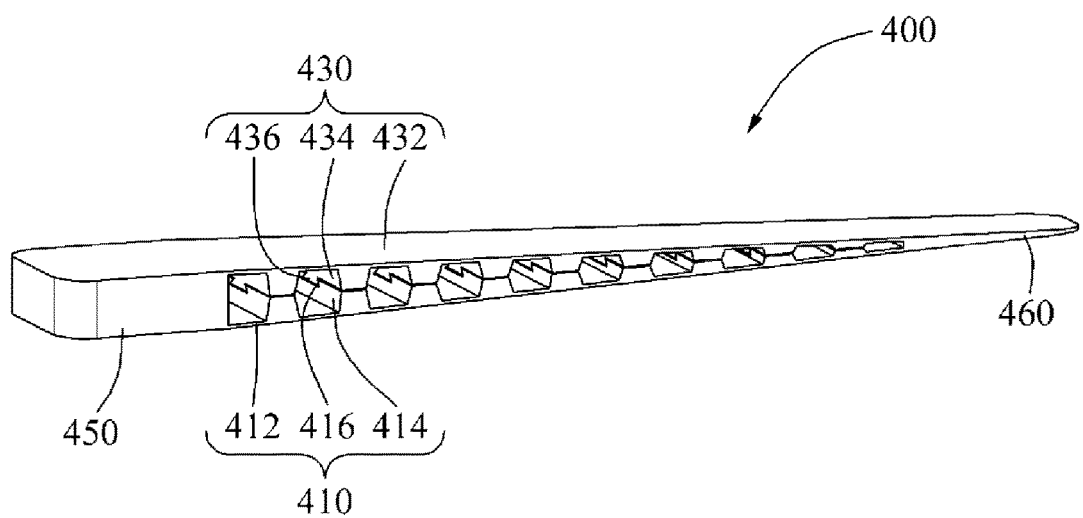
FIG. 11 is a perspective view illustrating a force transmitting frame according to some example embodiments.

FIG. 11 is a perspective view illustrating a force transmitting frame 400 according to some example embodiments.

Referring to FIG. 11, the force transmitting frame 400 may include an inner frame 410, an outer frame 430, a joint connecting portion 450, and an applying portion 460. The inner frame 410 may include an inner plate 412, a first protruding portion 414, and a first hanging portion 416. The outer frame 430 may include an outer plate 432, a second protruding portion 434, and a second hanging portion 436.

An interval between the inner plate 412 and the outer plate 432 may be determined based on Equation 6. For example, when the inner plate 412 has a shape of a straight line as shown in FIG. 11, a value of dp(x)/dx may be a constant. In some example embodiments, a value of h(x) may be proportional to a value of (L−x). Thus, the interval h(x) between the inner plate 412 and the outer plate 432 may increase from the applying portion 460 toward the joint connecting portion 450. A distance between the inner plate 412 and the outer plate 432 may increase as a distance from the applying portion 460 increases.

A width of the first protruding portion 414 may decrease as a distance from the inner plate 412 increases. A width of an upper side of the first protruding portion 414 may be smaller than a width of a lower side thereof. The first protruding portion 414 may have a slope of a taper shape. By the foregoing structure, when the second protruding portion 434 is inserted into an interval between two adjacent first protruding portions 414, the second protruding portion 434 may move along slopes of the first protruding portions 414, without being obscured by the first protruding portions 414.

Figure 12A:
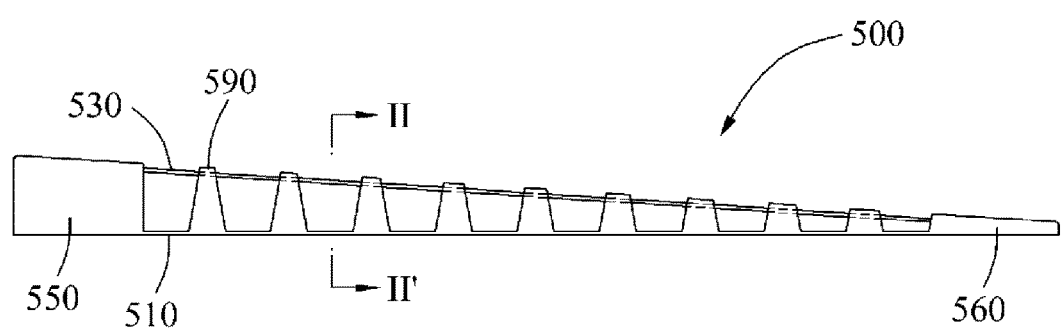
FIGS. 12A and 12B are views illustrating a force transmitting frame according to some example embodiments.
Figure 12B:
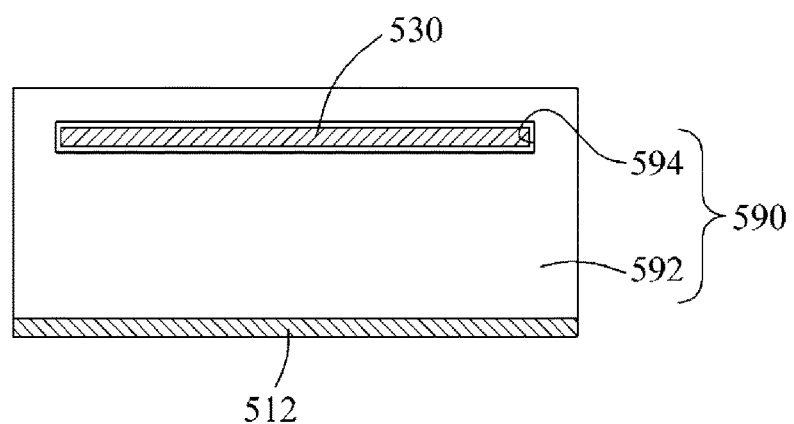

FIGS. 12A and 12B are views illustrating a force transmitting frame 500 according to some example embodiments.

Referring to FIGS. 12A and 12B, the force transmitting frame 500 may include an inner frame 510, an outer frame 530, a joint connecting portion 550, and an applying portion 560. The inner frame 510 may include an inner plate 512 and a guide portion 590.

One end of the inner plate 512 and one end of the outer frame 530 may be fixed to the joint connecting portion 550, and another end of the inner plate 512 and another end of the outer frame 530 may be fixed to the applying portion 560. A central portion of the outer frame 530 may slide with respect to a central portion of the inner plate 512.

The guide portion 590 may guide a movement of the outer frame 530. The guide portion 590 may include a guide protrusion 592 and a guide hole 594. The guide protrusion 592 may be formed to protrude from the inner plate 512. A plurality of guide protrusions 592 may be disposed to be spaced apart from each other in a longitudinal direction of the inner plate 512. Each guide protrusion 592 may be formed lengthwise in a direction orthogonal to the longitudinal direction of the inner plate 512. The guide hole 594 may be provided in the guide protrusion 592, and the outer frame 530 may be received in the guide hole 594. The guide hole 594 may enable the outer frame 530 to be spaced apart from the inner plate 512 at a desired interval (that may or may not be predetermined). For example, the guide hole 594 may be formed at a position of h(x) determined based on Equation 6.

Figure 13:
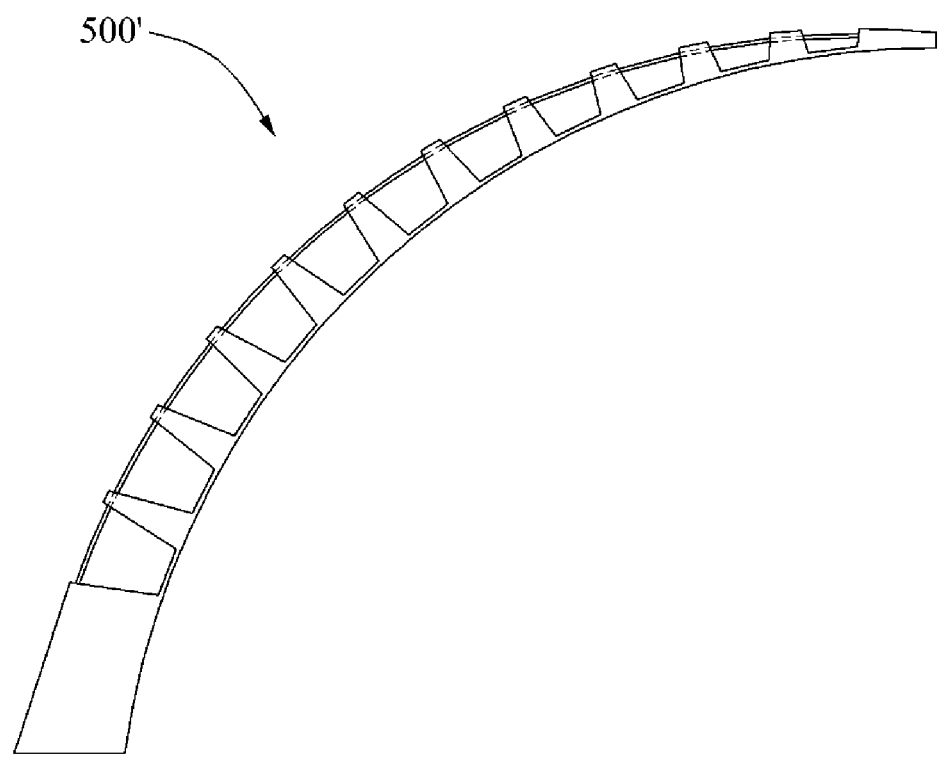
FIG. 13 is a side view illustrating a force transmitting frame according to some example embodiments.

Although FIGS. 12A and 12B illustrate the force transmitting frame 500 having a shape of a straight line, a force transmitting frame 500' may be provided in a bent shape as shown in FIG. 13, or in a shape in which a central area is bent and a portion is twisted, as shown in FIGS. 1 through 3.

Figure 14A:
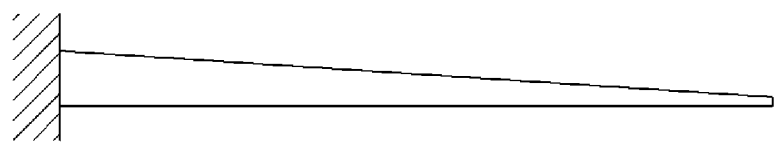
FIGS. 14A through 14C are views illustrating a force transmitting frame deformed when a load is applied to the force transmitting frame according to some example embodiments.
Figure 14B:
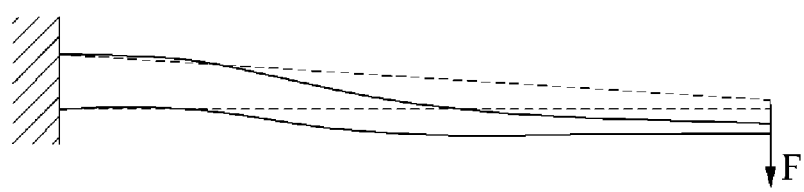
Figure 14C:
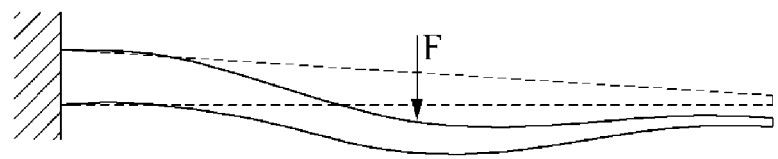

FIGS. 14A through 14C are views illustrating a force transmitting frame deformed when a load is applied to the force transmitting frame according to some example embodiments.

In detail, FIG. 14A illustrates a state in which a load is not applied to the force transmitting frame, FIG. 14B illustrates a state in which a load is applied to an applying portion of the force transmitting frame, and FIG. 14C illustrates a state in which a load is applied to a central portion of the force transmitting frame.

As described above, a stiffness of an end portion of the force transmitting frame may be greater than a stiffness of the central portion thereof. Thus, when a load F is applied to the end portion of the force transmitting frame, a location of the end portion of the force transmitting frame may not change greatly, as shown in FIG. 14B. However, when the identical load F is applied to the central portion of the force transmitting frame, a location of the central portion of the force transmitting frame may change greatly, as shown in FIG. 14C.

Figure 15:
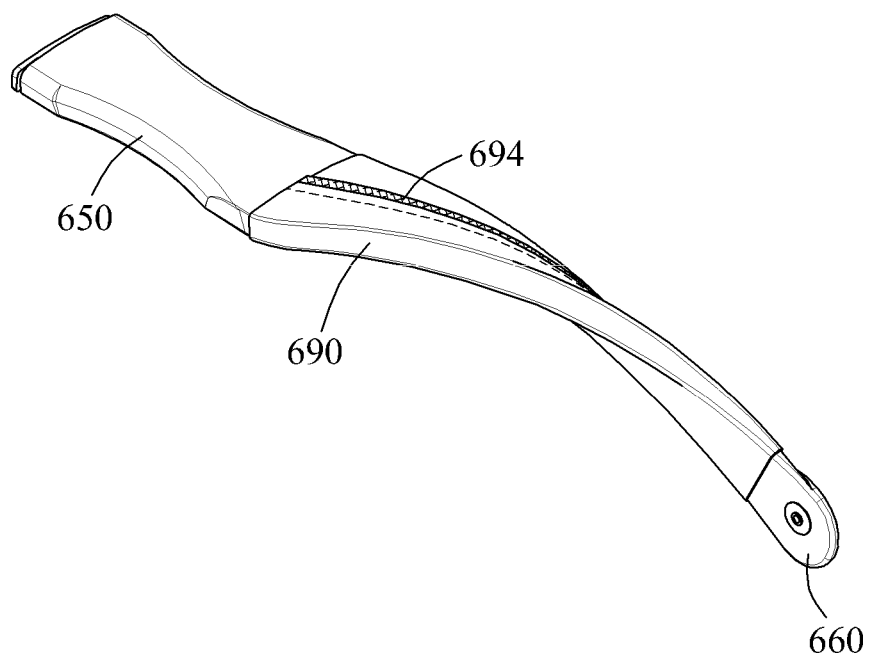
FIG. 15 is a view illustrating a force transmitting frame according to some example embodiments.
Figure 16:
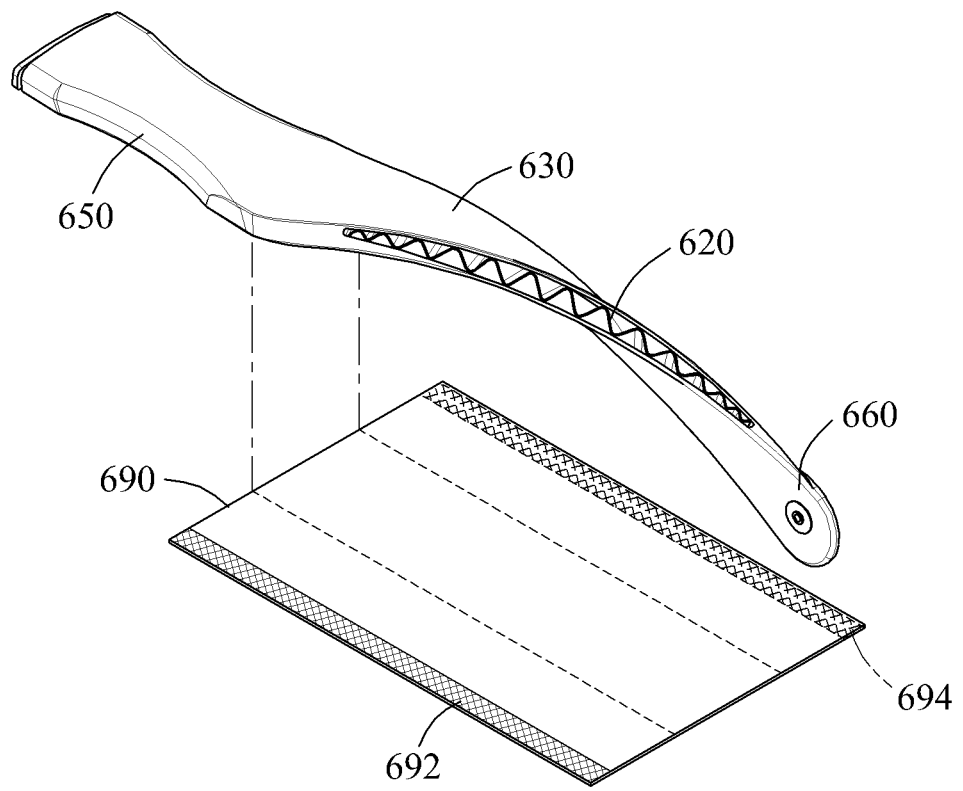
FIG. 16 is a view illustrating a state of a separation preventing band separating from a force transmitting frame according to some example embodiments.
Figure 17:
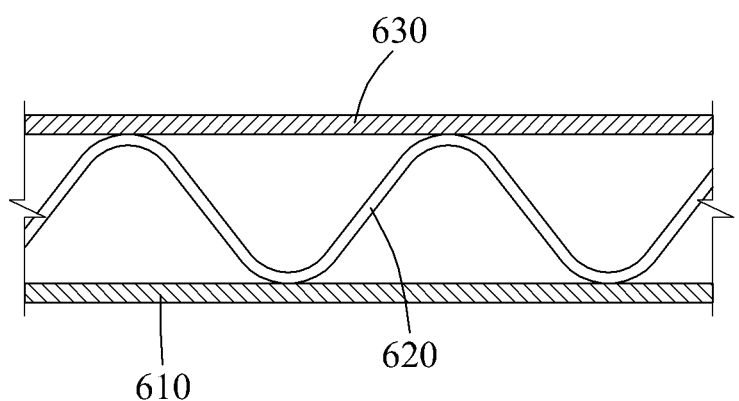
FIG. 17 is a view illustrating a supporting body according to some example embodiments.

FIG. 15 is a view illustrating a force transmitting frame 600 according to some example embodiments. FIG. 16 is a view illustrating a state of a separation preventing band 690 separating from the force transmitting frame 600 according to some example embodiments. FIG. 17 is a view illustrating a supporting body 620 according to some example embodiments.

Figure 18:
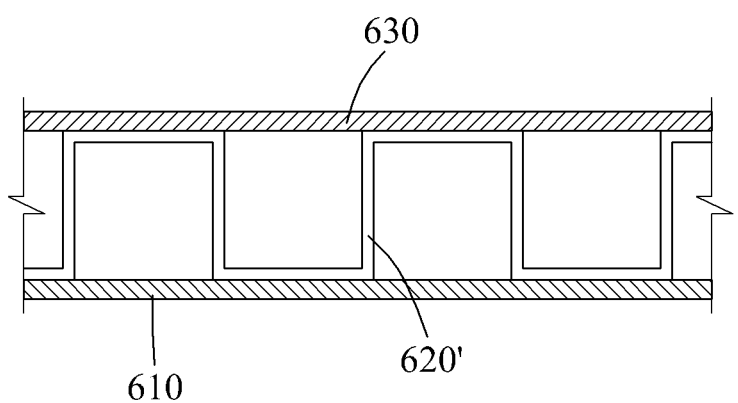
FIG. 18 is a view illustrating a supporting body based on a first transformation example according to some example embodiments.
Figure 19:
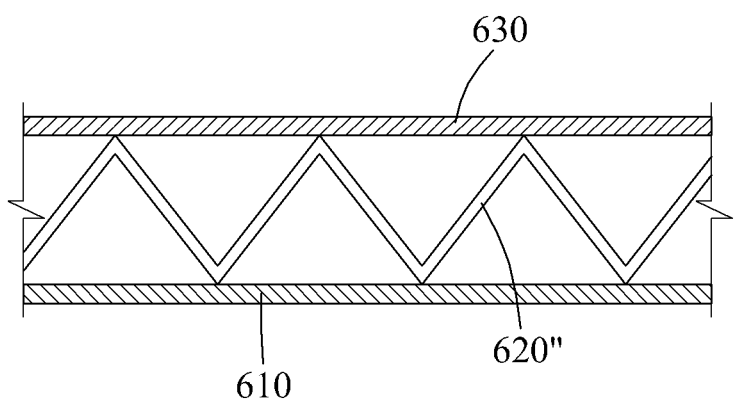
FIG. 19 is a view illustrating a supporting body based on a second transformation example according to some example embodiments.

FIG. 18 is a view illustrating the supporting body 620 based on a first transformation example according to some example embodiments. FIG. 19 is a view illustrating the supporting body 620 based on a second transformation example according to some example embodiments.

Referring to FIGS. 15-19, the force transmitting frame 600 may include an inner frame 610, an outer frame 630, the supporting body 620, the joint connection portion 650, the applying portion 660, and the separation preventing band 690. The inner frame 610 and the outer frame 630 may also be referred to as, for example, a first plate and a second plate, respectively.

The supporting body 620 may be inserted between the inner frame 610 and the outer frame 630 to support the inner frame 610 and the outer frame 630. The supporting body 620 may be formed of a carbon fiber material, for example, carbon fiber reinforced plastic (CFRP). The supporting body 620 may be vertically bent a plurality of times. For example, as illustrated in FIGS. 17-19, the supporting body 620 may be provided in a form of a sine wave (620), a square wave (620'), or a zigzag (620"). By using the supporting body 620, the inner frame 610 and the outer frame 630 may be maintained to be spaced apart from one another by at least a desired distance (that may or may not be predetermined).

The separation preventing band 690 may prevent a separation of the inner frame 610 and the outer frame 630 from one another. The separation preventing band 690 may be wound around circumferences of the inner frame 610 and the outer frame 630. The separation preventing band 690 may be formed of, for example, a fabric material. The separation preventing band 690 may include a first hook-and-loop fastener 692 and a second hook-and-loop fastener 694 on both sides, respectively, such that both sides of the separation preventing band 690 are fixed to each other.

A general longitudinal member including a flexible material may have a change increasing as a distance from a fixing end increases. Thus, force may not be transmitted properly at an end portion of the longitudinal member including the flexible material. A general longitudinal member including a stiff material may transmit force properly at an end portion thereof. However, a flexibility of the longitudinal member including the stiff material may decrease at a central portion thereof. Thus, the longitudinal member including the stiff material may have difficulty in handling changes in a volume of a user with respect to various motion states. In addition, frictional force with the user may increase. However, a force transmitting frame according to some example embodiments may include a flexible central portion and stiff end portions and, thus, the force transmitting frame may reduce a loss of force in a power transmitting process while reducing the frictional force with the user. Further, designing a frame to be spaced apart from a body to prevent a frictional issue may be unnecessary. Thus, a volume to be used to dispose the frame may be reduced, and the entire motion assistance apparatus may be worn under clothing. In addition, since relatively great torque may be transmitted at an end portion using relatively small force, the user may feel relatively small force on the skin and, thus, a user inconvenience may decrease.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to muscular strength assisting apparatuses, those skilled in the art will appreciate that some example embodiments may be applied to other types of systems, such as systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the muscular strength assisting apparatuses described in this application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A force transmitting frame having a length greater than a width, wherein stiffnesses of first and second end portions of the force transmitting frame are greater than a stiffness of a central area of the force transmitting frame in a longitudinal direction of the force transmitting frame, the force transmitting frame comprising:
   an inner frame configured to support one side of a user; and
   an outer frame of which first and second end portions are fixed to first and second end portions of the inner frame, respectively, and of which a central portion is not fixed to a central portion of the inner frame, wherein
      the central portion of the outer frame is configured to slide with respect to the central portion of the inner frame.

2. The force transmitting frame of claim 1, wherein the central area is flexible.

3. The force transmitting frame of claim 1, wherein the stiffnesses of the first and second end portions are 1.5 to 20 times greater than the stiffness of the central area.

4. The force transmitting frame of claim 1, wherein the stiffnesses of the first and second end portions are 4 to 10 times greater than the stiffness of the central area.

5. The force transmitting frame of claim 1, wherein surfaces of the first and second end portions face a same direction.

6. The force transmitting frame of claim 1, wherein surfaces of the first and second end portions face different directions.

7. The force transmitting frame of claim 6, wherein the surfaces of the first and second end portions form an angle of 80 degrees to 100 degrees.

8. The force transmitting frame of claim 1, wherein
   the inner frame comprises an inner plate and a first hanging portion between the inner plate and an outer plate, and
   wherein the outer frame comprises the outer plate and a second hanging portion configured to fasten to the first hanging portion.

9. The force transmitting frame of claim 8, wherein one of the first hanging portion and the second hanging portion comprises a portion having a width increasing in a direction toward the other of the first hanging portion and the second hanging portion.

10. The force transmitting frame of claim 9, wherein a cross-section of the one hanging portion corresponds to a reversed trapezoidal shape.

11. The force transmitting frame of claim 8, wherein
    the inner frame further comprises a first protruding portion configured to protrude from the inner plate toward the outer plate, and
    wherein the outer frame further comprises a second protruding portion configured to protrude from the outer plate toward the inner plate.

12. The force transmitting frame of claim 11, wherein
    a plurality of first protruding portions are formed in a longitudinal direction of the inner frame, and
    wherein a plurality of second protruding portions are formed in a longitudinal direction of the outer frame.

13. The force transmitting frame of claim 12, wherein an interval between two adjacent first protruding portions, among the plurality of first protruding portions, is configured to be shorter than a length of a second protruding portion provided on an opposite side of the two first protruding portions.

14. The force transmitting frame of claim 8, wherein an interval between the inner plate and the outer plate decreases from the central area of the force transmitting frame toward the first and second end portions of the force transmitting frame.

15. The force transmitting frame of claim 8, wherein an interval between the inner plate and the outer plate is determined based on the following Equation, $$h(x) = \frac{F(L-x)}{T - F\sin\left(\operatorname{atan}\left(\frac{d}{dx}p(x)\right)\right)} \quad [\text{Equation}]$$

wherein 'h(x)' denotes the interval between the inner plate and the outer plate, 'F' denotes a magnitude of a force applied to one end portion of the force transmitting frame, 'T' denotes a magnitude of a tensile force applied to the inner plate, 'L' denotes a length of the force transmitting frame, 'x' denotes a distance from an end portion of the force transmitting frame to a desired point of the inner plate, and 'p(x)' denotes a height of the inner plate at the distance x.

16. The force transmitting frame of claim 8, further comprising:
    an applying portion connected to one end of the inner frame and one end of the outer frame, and configured to transmit a force to a portion of the user.

17. The force transmitting frame of claim 16, wherein a thickness of the applying portion is configured to be greater than a sum of a thickness of the one end of the inner frame and a thickness of the one end of the outer frame.

18. The force transmitting frame of claim 16, wherein a distance between the inner plate and the outer plate increases as a distance from the applying portion increases.

19. The force transmitting frame of claim 1, further comprising:
a frame stiffener provided on at least one of the inner frame and the outer frame.

20. The force transmitting frame of claim 19, wherein the frame stiffener comprises a carbon fiber material.

21. The force transmitting frame of claim 1, further comprising:
a supporting body, between the inner frame and the outer frame, configured to support the inner frame and the outer frame; and
a separation preventing band configured to prevent separation of the inner frame and the outer frame from one another.

22. The force transmitting frame of claim 21, wherein the supporting body is vertically bent a plurality of times,
wherein the supporting body comprises carbon fiber,
wherein the separation preventing band is wound around circumferences of the inner frame and the outer frame, and
wherein the separation preventing band comprises fabric material.

23. The force transmitting frame of claim 1, wherein
the inner frame includes a first plate,
the outer frame includes a second plate, wherein
the central area between the first and second end portions is configured to prevent separation of the first plate from the second plate.

24. The force transmitting frame of claim 23, wherein the central area is part of the first plate.

25. A force transmitting frame having a length greater than a width, wherein
stiffnesses of first and second end portions of the force transmitting frame are greater than a stiffness of a central area of the force transmitting frame in a longitudinal direction of the force transmitting frame, and
the central area is provided in a form of a twisted curve.

26. A force transmitting frame, comprising:
a first plate;
a second plate configured to face the first plate;
a connecting portion configured to connect a first end of the first plate to a first end of the second plate; and
an applying portion configured to connect a second end of the first plate to a second end of the second plate, wherein
the first end and the second end of the second plate are fixed to the first end and the second end of the first plate, respectively,
a central portion of the second plate is not fixed to a central portion of the first plate, and
the central portion of the second plate is configured to slide with respect to the central portion of the first plate.

27. The force transmitting frame of claim 26, further comprising:
a separation preventing member configured to prevent separation between the first plate and the second plate.

28. The force transmitting frame of claim 27, wherein a first side of the separation preventing member is slidingly connected to the first plate, and a second side of the separation preventing member is slidingly connected to the second plate.

29. The force transmitting frame of claim 26, further comprising:
a guide portion comprising a guide protrusion configured to protrude from the first plate, and a guide hole provided in the guide protrusion, wherein
the second plate is configured to be received in the guide hole.

30. The force transmitting frame of claim 26, wherein an interval between the first plate and the second plate is determined in proportion to a value obtained by multiplying an inner product of a first unit vector of a normal direction of the applying portion and a second unit vector of a direction of the interval by a distance value from the applying portion to the interval.

31. The force transmitting frame of claim 26, wherein an interval between the first plate and the second plate is determined in proportion to a distance in a direction perpendicular to a direction of a force applied to the applying portion.

32. The force transmitting frame of claim 26, further comprising:
a supporting body, between the first plate and the second plate, configured to support the first plate and the second plate; and
a separation preventing band configured to prevent separation of the first plate and the second plate from one another.

33. A motion assistance apparatus, comprising:
a fixing member to be attached to a user;
a driving source provided on one side of the fixing member;
a joint assembly configured to assist rotary motion of a joint portion of the user; and
a force transmitting frame of which a first end portion is connected to the joint assembly, and of which a second end portion is configured to transmit a force to a portion of the user, wherein
a stiffness of the second end portion of the force transmitting frame is greater than a stiffness of a central portion of the force transmitting frame,
the force transmitting frame includes first and second plates,
first and second end portions of the first plate are fixed to first and second end portions of the second plate, respectively,
a central portion of the first plate is not fixed to a central portion of the second plate, and
the central portion of the first plate is configured to slide with respect to the central portion of the second plate.

34. The motion assistance apparatus of claim 33, wherein the stiffness of the second end portion of the force transmitting frame is 1.5 to 20 times greater than the stiffness of the central portion of the force transmitting frame.

35. The motion assistance apparatus of claim 33, wherein the stiffness of the second end portion of the force transmitting frame is 4 to 10 times greater than the stiffness of the central portion of the force transmitting frame.

36. The motion assistance apparatus of claim 33, wherein the force transmitting frame further comprises:
a supporting body, between the first and second plates, configured to support the first and second plates; and
a separation preventing band configured to prevent separation of the first and second plates from one another.

* * * * *